United States Patent [19]
Smith et al.

[11] Patent Number: 5,621,780
[45] Date of Patent: Apr. 15, 1997

[54] X-RAY APPARATUS FOR APPLYING A PREDETERMINED FLUX TO AN INTERIOR SURFACE OF A BODY CAVITY

[75] Inventors: Donald O. Smith, Lexington; Alan P. Sliski, Lincoln; Kenneth J. Harte, Carlisle, all of Mass.

[73] Assignee: Photoelectron Corporation, Lexington, Mass.

[21] Appl. No.: 507,845

[22] Filed: Jul. 27, 1995

Related U.S. Application Data

[63] Continuation of Ser. No. 273,645, Jul. 12, 1994, abandoned, which is a continuation-in-part of Ser. No. 184,271, Jan. 21, 1994, Pat. No. 5,422,926, which is a continuation-in-part of Ser. No. 955,494, Oct. 2, 1992, Pat. No. 5,369,679, which is a continuation-in-part of Ser. No. 577,883, Sep. 5, 1990, Pat. No. 5,153,900.

[51] Int. Cl.⁶ .................................................. H01J 35/32
[52] U.S. Cl. .......................... 378/65; 378/119; 378/145; 128/659; 604/20
[58] Field of Search ........................... 378/64, 65, 145, 378/119, 140; 604/20, 21; 128/658, 659

[56] References Cited

U.S. PATENT DOCUMENTS

| | | | |
|---|---|---|---|
| 2,799,273 | 7/1957 | Oddo . | |
| 2,849,002 | 8/1958 | Oddo . | |
| 3,752,990 | 8/1973 | Fischer | 378/119 |
| 4,143,275 | 3/1979 | Mallozzi et al. | 378/119 |
| 4,470,407 | 9/1984 | Hussein | 128/6 |
| 4,608,977 | 9/1986 | Brown | 378/208 |
| 4,646,338 | 2/1987 | Skillicorn | 378/110 |
| 4,694,480 | 9/1987 | Skillicorn | 378/119 |
| 4,932,958 | 6/1990 | Reddy et al. | 606/192 |
| 5,002,558 | 3/1991 | Klein et al. | 606/192 |
| 5,007,897 | 4/1991 | Kalb et al. | 604/43 |
| 5,090,043 | 2/1992 | Parker et al. | 378/65 |
| 5,153,900 | 10/1992 | Nomiko et al. | 378/65 |
| 5,165,093 | 11/1992 | Miller et al. | 378/138 |
| 5,209,725 | 5/1993 | Roth | 606/191 |
| 5,369,679 | 11/1994 | Sliski et al. | 378/65 |

FOREIGN PATENT DOCUMENTS

| | | |
|---|---|---|
| 63-221078 | 5/1990 | Japan . |
| 2-68073 | 5/1993 | Japan . |

OTHER PUBLICATIONS

Nseyo et al., *Urology* (1990) vol. XXXVI, No. 5, "Whole Bladder Photodynamic Therapy: Critical Review of Present-Day Technology and Rationale For Development Of Intravesical Laser Catheter and Monitoring System", pp. 398–402. No Month.

*Primary Examiner*—Don Wong
*Attorney, Agent, or Firm*—Lappin & Kusmer

[57] ABSTRACT

The present invention is directed to an x-ray source for irradiating a surface defining a body cavity in accordance with a predetermined dose distribution. The source comprises a housing, an elongated tubular probe, a target assembly, and an inflatable balloon. The housing encloses an electron beam source and includes elements for generating an electron beam along a beam path. The tubular probe extends along a central axis from the housing about the beam path. The target assembly extends along the central axis and is coupled to the end of the probe distal from the housing. The target assembly includes a target element is positioned in the beam path. The target element is adapted to emit x-rays in response to electrons incident thereon from the beam. The probe tip assembly and associated control electronics include elements for positioning the target element in the beam path, and is substantially x-ray transparent. The balloon is affixed to the distal end of the probe and is inflatable so that when that probe end is inserted into a body cavity, the balloon may be inflated to stretch the cavity to a known shape. Positioning the probe tip inside the inflated balloon allows delivery of a uniform, or other desired, dose of radiation to the surface defining a body cavity.

24 Claims, 7 Drawing Sheets

X-RAY APPARATUS FOR APPLYING A PREDETERMINED FLUX TO AN INTERIOR SURFACE OF A BODY CAVITY

This is a continuation of application Ser. No. 08/273,645 filed on Jul. 12, 1994 now abandoned which is a continuation-in-part of U.S. patent application Ser. No. 08/184,271, entitled X-RAY SOURCE WITH SHAPED RADIATION PATTERN, filed Jan. 21, 1994, assigned to the assignee of the present application, U.S. Pat. No. 5,422,926 which is a continuation-in-part of U.S. patent application Ser. No. 07/955,494, entitled LOW POWER X-RAY SOURCE WITH IMPLANTABLE PROBE FOR TREATMENT OF BRAIN TUMORS, filed Oct. 2, 1992, U.S. Pat. No. 5,369,679 assigned to the assignee of the present application, which is a continuation-in-part of U.S. patent application Ser. No. 577,883, now U.S. Pat. No. 5,153,900, entitled MINIATURIZED LOW POWER X-RAY SOURCE, filed Sep. 5, 1990, assigned to the assignee of the present application.

BACKGROUND OF DISCLOSURE

The present invention relates to a miniaturized, low power, programmable x-ray source for use in delivering substantially constant or intermittent levels of x-rays to a specified region. More specifically, the invention relates to apparatus and methods for delivering a uniform x-ray flux to an interior surface of a body cavity.

Most conventional medical x-ray sources are large, fixed position machines. Generally, the head of the x-ray tube is placed in one room and the control console in an adjoining area, with a protective wall, equipped with a viewing window, separating the two. The x-ray tube typically is approximately 20 to 35 centimeters (cm) long, and approximately 15 cm in diameter. A high voltage power supply is housed within a container located in a corner of the room containing the x-ray tube. Patients are brought to the machine for diagnostic, therapeutic, or palliative treatment.

Diagnostic x-ray machines are typically operated at voltages below 150 kilovolts (kV), and at currents from approximately 25 to 1200 milliamps (mA). By contrast, the currents in therapeutic units typically do not exceed 20 mA at voltages which may range above 150 kV. When an x-ray machine is operated at nominal voltages of 10 to 140 kV, the emitted x-rays provide limited penetration of tissue, and are thus useful in treating skin lesions. At higher voltages (approximately 250 kV), deep x-ray penetration is achieved, which is useful in the treatment of major body tumors. Super voltage machines, operable in the 4 to 8 megavolt (MV) region, are used to ablate or destroy all types of tumors, except superficial skin lesions.

A conventional x-ray tube includes an anode, grid, and cathode assembly. The cathode assembly generates an electron beam which is directed to a target, by an electric field established by the anode and grid. The target in turn emits x-ray radiation in response to the incident electron beam. The radiation absorbed by a patient generally is that which is transmitted from the target in the x-ray tube through a window in the tube, taking into account transmission losses. This window typically is a thin section of beryllium, or other suitable material. In a typical x-ray machine, the cathode assembly consists of a thoriated tungsten coil approximately 2 mm in diameter and 1 to 2 cm in length which, when resistively heated with a current of 4 amps (A) or higher, thermionically emits electrons. This coil is surrounded by a metal focusing cup which concentrates the beam of electrons to a small spot on an opposing anode which also functions as the target. In models having a grid, it is the grid which both controls the path of the electron beam and focuses the beam.

The transmission of an electron beam from cathode to anode is influenced by electron space charge forces which tend to become significant in conventional x-ray machines at currents exceeding 1 A. In such conventional machines, the beam is focused on the anode to a spot diameter ranging anywhere from 0.3 to 2.5 millimeters (mm). In many applications, most of the energy from the electron beam is converted into heat at the anode. To accommodate such heating, high power medical x-ray sources often utilize liquid cooling and a rapidly rotating anode, thereby establishing an increased effective target area, permitting a small focal spot while minimizing the effects of localized heating. To achieve good thermal conductivity and effective heat dissipation, the anode typically is fabricated from copper. In addition, the area of the anode onto which an electron beam is incident requires a material of high atomic number for efficient x-ray generation. To meet the requirements of thermal conductivity, effective heat dissipation, and efficient x-ray generation, a tungsten alloy typically is embedded in the copper.

In use, the total exposure from an x-ray source is directly proportional to the time integral of the electron beam. During relatively long exposures (e.g. lasting 1 to 3 seconds), the anode temperature may rise sufficiently to cause it to glow brightly, accompanied by localized surface melting and pitting which degrades the radiation output. However, thermal vaporization of the tube's coiled cathode filament is most frequently responsible for conventional tube failure.

While the efficiency of x-ray generation is independent of the electron beam current, it is highly dependent on the acceleration voltage. Below 60 kV, only a few tenths of one percent of the kinetic energy from an electron is converted to x-rays, whereas at 20 MV that conversion factor rises to 70 percent. An emitted x-ray spectrum is composed in part of discrete energies characteristic of transitions between bound electron energy levels of the target element. The spectrum also includes an x-ray energy continuum, known as bremsstrahlung, which is caused by acceleration of the beam electrons as they pass near target nuclei. The maximum energy of an x-ray cannot exceed the peak energy of an electron in the beam. Further, the peak of the bremsstrahlung emission curve occurs at approximately one-third the electron energy.

Increasing the electron current results in a directly proportional increase in x-ray emission at all energies. However, a change in beam voltage results in a total x-ray output variation approximately equal to the square of the voltage, with a corresponding shift in peak x-ray photon energy. The efficiency of bremsstrahlung radiation production increases with the atomic number of the target element. The peak output in the bremsstrahlung curve and the characteristic spectral lines shift to higher energies as the atomic number of the target increases. Although tungsten (Z=74) is the most common target material used in modern tubes, gold (Z=79) and molybdenum (Z=42) are used in some specialty tubes.

One disadvantage of most x-ray devices used for therapy is the high voltage, and consequent high energy radiation required when directed to soft tissue within or beneath bone. One example is in directing x-rays to areas of the human brain, which is surrounded by bone. High energy x-rays are required to penetrate the bone, but often damage the skin and brain tissue between the radiation entry site and the tumor. Another example in radiation therapy is in directing the x-rays to soft tissue located within the body cavity, couched among other soft tissue, or within an internal calciferous structure. Present high-voltage x-ray machines are limited in their ability to selectively provide desired x-ray radiation to such areas.

Another disadvantage of the conventional high voltage x-ray sources is the damage caused to skin external to the affected organ or tissue. Therefore, prior art high voltage x-ray sources often cause significant damage not only to the target region or tissue, but also to all surrounding tissue between the entry site, the target region, and the exit site, particularly when used for human tumor therapy. However, since present devices apply x-ray radiation to target regions internal to a patient from a source external to the target region, such incidental tissue damage is practically unavoidable.

Conventional radiation treatment of the soft tissue that lines body cavities, such as the bladder, vagina and cervix, urethra, uterus, colon and rectum, involves application of x-radiation from an extracorporeal source. Consequently, such techniques of radiation therapy have the disadvantage that they necessarily radiate areas of the patient between the radiation entry site, the target tissue, and the exit site, causing damages to such tissue.

Conventional methods of radiation treatment for body cavities also have the further disadvantage of failing to provide the ability to establish a uniform dose of radiation to the target tissue. In some cases, it is desirable that radiation treatment of the tissue lining a body cavity should provide the same dose of radiation to every segment of the tissue, i.e., a uniform, or other desired, dose. In other cases, specifically contoured non-uniform doses may be desired. The prior art x-ray sources cannot accomplish this for interior body cavities. As used herein, the term "uniform dose" refers to an isodose contour, i.e., a surface over which the flux density is substantially constant.

Some of these disadvantages can be overcome through the use of miniaturized low power x-ray sources, such as the one described in the above-referenced U.S. Pat. No. 5,153,900 issued to Nomikos et al. These sources can be inserted into, and activated from within, a patient's body. Thus, these sources can generate x-rays local to the target tissue. When such x-ray sources are used to treat the tissue lining a body cavity, the x-rays need not pass through the patient's skin, bone and other tissue prior to reaching the target tissue. However, even utilizing these sources there is no previously known method of providing a uniform, or other desired, dose of radiation to the target tissue, particularly where the geometry of the target region is not fixed, for example, as in the bladder which has a flexible inner wall without a well-defined shape.

By way of example, some miniature sources of the type disclosed in U.S. Pat. No. 5,153,900 generally act as point sources of x-ray radiation. Therefore, the strength of the radiation field decreases uniformly in air with approximately the square of the distance from the source (i.e., $1/R^2$). Since body cavities are not generally spherically symmetrical, a point source within a body cavity will not deliver a uniform dose of radiation to the tissue lining the cavity.

It is therefore an object of the invention to provide a method and apparatus for delivering a uniform dose of radiation to the tissue that lines a body cavity.

It is a further object of the invention to provide an apparatus, that includes a miniature low power x-ray source, for delivering a uniform or other desired dose of radiation to the tissue that lines a body cavity.

Other objects and advantages of the present invention will become apparent upon consideration of the appended drawings and description thereof.

SUMMARY OF THE INVENTION

In one form, the invention is a kit for applying a predetermined x-ray flux to an interior surface of a body cavity including an x-ray source, intended for insertion into the cavity, and an inflatable balloon assembly.

The x-ray source includes a tubular element, a beam source, and a controller. The tubular element has a target end that contains an electron activated x-ray source. The beam source is disposed near a beam source end of the tubular element and is operative to generate an electron beam. The controller selectively activates the beam source such that the electron beam is incident on the target end. The target end of the x-ray source is positioned within the body cavity-to-be-irradiated.

The balloon assembly includes an inflatable balloon positioned at the target end of the tubular element of the x-ray source. When inflated, the balloon defines an interior region adjacent to the target end.

With this configuration, the balloon may be inflated so that it is in contact with the lining of the body cavity, and displaces that cavity to define a desired shape for that lining. The target end is positioned within the interior region defined by the inflated balloon. By way of example, the balloon may be positioned with a bladder of a patient and, when inflated, it may define a spherical interior region and the target may be positionable at the center of the sphere. Also according to this aspect, the electron activated x-ray source may generate an x-ray field having an isodose contour coincident with the surface of the inflated balloon, thereby providing a uniform dose to the lining of the bladder.

Thus, with the invention, a surface of a body cavity is conformed to a predetermined contour and then the x-ray source is adjusted to establish a uniform dose at that surface (i.e., an isodose contour, over which the flux density is substantially constant). The flux density decreases with distance from the source beyond the cavity lining, permitting treatment of the lining surface and diminishing effects in tissue beyond that lining.

BRIEF DESCRIPTION OF DRAWINGS

The foregoing and other objects of this invention, the various features thereof, as well as the invention itself, may be more fully understood from the following description, when read together with the accompanying drawings in which.

Like numbered elements in each FIGURE represent the same or similar elements.

DESCRIPTION OF THE PREFERRED EMBODIMENTS

The present invention is a relatively small, electron-beam activated, low power x-ray kit and a method of use of such kit. The kit may be used for medical purposes such as therapeutic radiation of the soft tissue lining body cavities, for example, the bladder or other cavities.

Generally, the apparatus of the present invention includes an electron-beam (e-beam) activated x-ray source which operates at relatively low voltages, i.e. in the range of approximately 10 kV to 90 kV, and relatively small electron beam currents, i.e. in the range of approximately 1 nA to 1 mA. At those operating voltages and currents, the x-ray source may be made quite small and be adapted for implantation in medical therapeutic applications. Adequate tissue penetration and dosage may be attained by locating the x-ray source adjacent to or within the region to be irradiated. Thus, the x-rays are emitted from a well-defined, small source located within or adjacent to the region to be irradiated.

Figure 1:
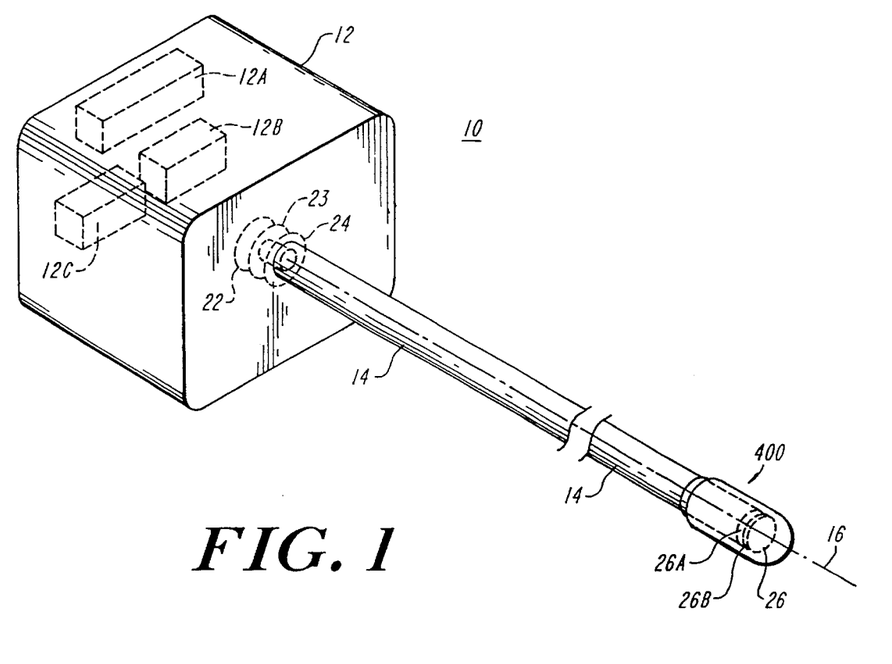
FIG. 1 is a perspective view of a kit embodying the present invention.

FIG. 1 shows an x-ray kit embodying the present invention. That kit includes an x-ray source 10 and a balloon assembly 400. A suitable x-ray source 10 is described in detail in the above referenced U.S. Pat. No. 5,153,900, entitled "Miniaturized Low Power X-Ray Source. The balloon assembly 400 is described in detail below in conjunction with FIGS. 5, 6 and 7.

X-ray source 10 includes a housing 12 and an elongated cylindrical probe 14 extending from housing 12 along a reference axis 16 and having a target assembly 26 at its distal end. The housing 12 encloses a high voltage power supply 12A. The probe 14 is a hollow tube having an electron beam generator (cathode) 22 adjacent to the high voltage power supply 12A. Cathode 22 is located in close proximity to an annular focusing electrode 23 typically at nearly the same potential as the cathode 22. An annular anode 24 is positioned approximately 0.5 cm or more from the annular focusing electrode 23. A hollow, tubular probe 14 extends along the same axis as the cathode, grid, and the hole in the anode. Probe 14 is integral with the housing 12 and extends toward a target assembly 26. In various embodiments, parts of the probe 14 may be selectively shielded to control the spatial distribution of x-rays. In addition, the probe 14 may be magnetically shielded to prevent external magnetic fields from deflecting the beam away from the target.

The electron beam generator 22 may include a thermionic emitter (driven by a floating low voltage power supply) or a photocathode (irradiated by an LED or laser source). The high voltage power supply establishes an acceleration potential difference between the cathode of generator 22 and the grounded anode 24 so that an electron beam is established along the reference axis 16, through the center hole of the anode and to the target assembly 26, with the region between anode 24 and the target assembly 26 being substantially field free. The beam generation and acceleration components are adapted to establish a thin (e.g. 1 mm or less in diameter) electron beam within the probe 14 along a nominally straight axis 16.

In a preferred embodiment, the probe 14 is a hollow, evacuated cylinder made of a beryllium (Be) cap and a molybdenum-rhenium, (Mo-Re), molybdenum (Mo) or mu-metal body and a stainless-steel base extension. The cylinder has a length which is determined in view of the cavity to be treated. For example, for use with a bladder, the probe may be 40 cm in length, with an interior diameter of 4 mm, and an exterior diameter of 5 mm. For use with other cavities, different geometries may be used.

The target assembly 26 includes an emission element consisting of a small beryllium (Be) window 26A coated on the side exposed to the incident electron beam with a thin film or layer 26B of a high-Z element, such as tungsten (W), uranium (U) or gold (Au). By way of example, with electrons accelerated to 30 keV-, a 2.2 micron thick tungsten film absorbs substantially all the incident electrons, while transmitting approximately 95% of any 30 keV-, 88% of any 20 keV-, and 83% of any 10 keV- x-rays generated in that layer. In the preferred embodiment, the beryllium widow 26A is 0.5 mm thick with the result that 95% of these x-rays generated in the layer 26B in directions normal to and toward the window, and having passed through the tungsten target layer 26B, are then transmitted through the beryllium window 26A and outward at the distal end of probe 14.

The apparatus of FIG. 1 is normally used in a manner where only the probe 14 is inserted into a patient while the housing remains outside the patient. In this form, some or all of the various elements shown within housing 12 may alternatively be remotely located.

In one embodiment of the apparatus as shown in FIG. 1, the main body of the probe 14 can be made of a magnetically shielding material such as a mu-metal. Alternatively, the probe 14 can be made of a non-magnetic metal, preferably having relatively high values for Young's modulus and elastic limit. Examples of such material include molybdenum, rhenium or alloys of these materials. The inner or outer surface of probe 14 can then be coated with a high permeability magnetic alloy such as permalloy (approximately 80% nickel and 20% iron), to provide magnetic shielding. Alternatively, a thin sleeve of mu-metal can be fitted over, or inside of, the probe 14. The x-ray apparatus 10 can then be used in environments in which there are low-level dc and ac magnetic fields due to electrical power, the field of the earth, or other magnetized bodies nominally capable of deflecting the electron beam from the probe axis.

In the above-described embodiments, the x-ray emission element of the target assembly 26 is adapted to be adjacent to or within the region of a patient to be irradiated. The proximity of the emission element to the targeted region, e.g. the body cavity, eliminates the need for the high voltages of presently used machines, to achieve satisfactory x-ray penetration through the body wall to the body cavity. The low voltage also concentrates the radiation in the targeted tissue, and limits the damage to surrounding tissue and surface skin at the point of entry.

Generally, when treating a body cavity with radiation therapy, it is desirable to uniformly radiate the entire surface of the soft tissue lining the cavity such that an isodose contour is coincident with the surface of the body cavity. An isodose contour is a surface in which the absorbed radiation energy is equal at every point on the surface.

A preferred method of uniformly radiating a body cavity, such as the bladder of a patient, is to use a device to first stretch the cavity into a spherical shape, and then position an omnidirectional x-ray generating probe tip (i.e., a point source) at the center of the cavity. With that configuration, an isodose contour can be established which is coincident with the surface of the body cavity. One device useful for stretching a body cavity to a spherical shape is an inelastic balloon.

Figure 2:
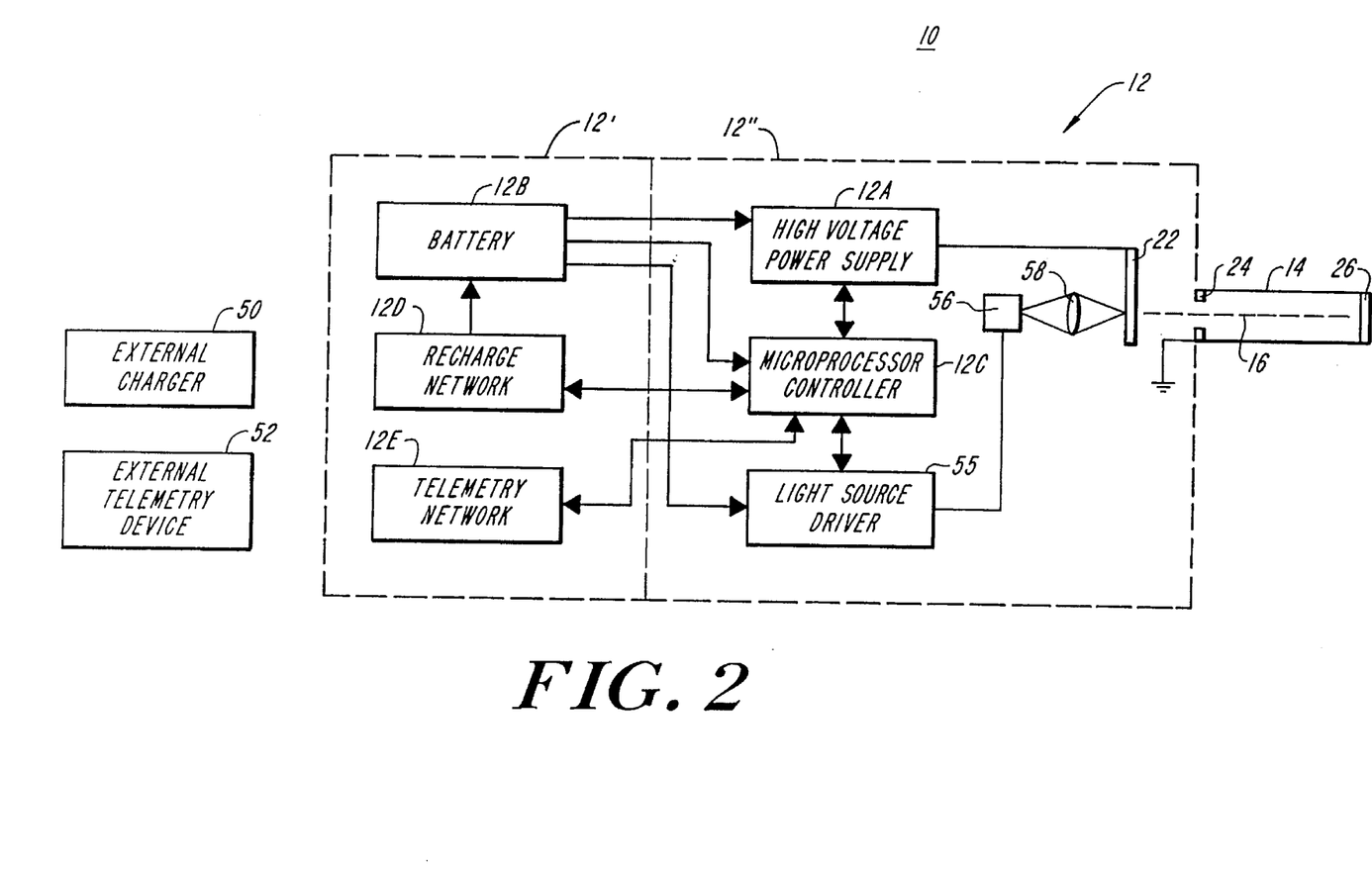
FIG. 2 is a schematic block diagram of the x-ray source of FIG. 1.

FIG. 2 is a block diagram representation of the x-ray source apparatus 10 shown in FIG. 1. In that preferred configuration, the housing 12 is divided into a first portion 12' and a second portion 12". Enclosed within the first housing portion 12' is a rechargeable battery 12B, a recharge network 12D for the battery 12B, which is adapted for use with an external charger 50, and a telemetry network 12E, adapted to be responsive to an external telemetry device 52 to function in the manner described below. That portion 12' is coupled by cables to the second housing portion 12". The second housing portion 12" includes the high voltage power supply 12A, controller 12C and the probe 14, as well as the electron beam generating element 22. In the illustrated embodiment, the electron beam generator includes a photoemitter 22 irradiated by a light source 56, such as a diode laser or LED, powered by a driver 55. The light is focused on the photoemitter 22 by a focusing lens 58.

In the illustrated embodiment, device 52 and network 12E cooperate to permit external control (dynamic or predetermined) control over the power supply 12A and temporal parameters. Controller 12C may directly be used to control operation in which case there is no need for network 12E.

In an alternate form, the beam generator may include a thermionic emitter 22 driven by the power supply 12A. In operation of that form, power supply 12A heats the thermionic emitter 22, which in turn generates electrons which are then accelerated toward the anode 24. The anode 24 attracts the electrons, but passes them through its central aperture toward the target assembly 26. The controller 12C controls the power supply 12A to dynamically adjust the cathode voltage, the electron beam current, and temporal parameters, or to provide pre-selected voltage, beam current, and temporal parameters. Other suitable power supply configurations are disclosed in U.S. Pat. No. 5,153,900 and in parent U.S. patent application Ser. No. 955,494.

Incident electrons generally cause target 26 to act as a point source of x-rays. However, further specificity in treating the surfaces body cavities, and of tumors on or adjacent to such surfaces, may be achieved by tailoring the target and shield geometry and material at the emission site. This tailoring facilitates the control of energy and the spatial profile of the x-ray emission to ensure more homogenous distribution of the radiation throughout the targeted body cavity. This tailoring is described in detail in the above referenced U.S. patent application Ser. No. 08/084,271, entitled "X-ray Source with Shaped Radiation Pattern".

Figure 3:
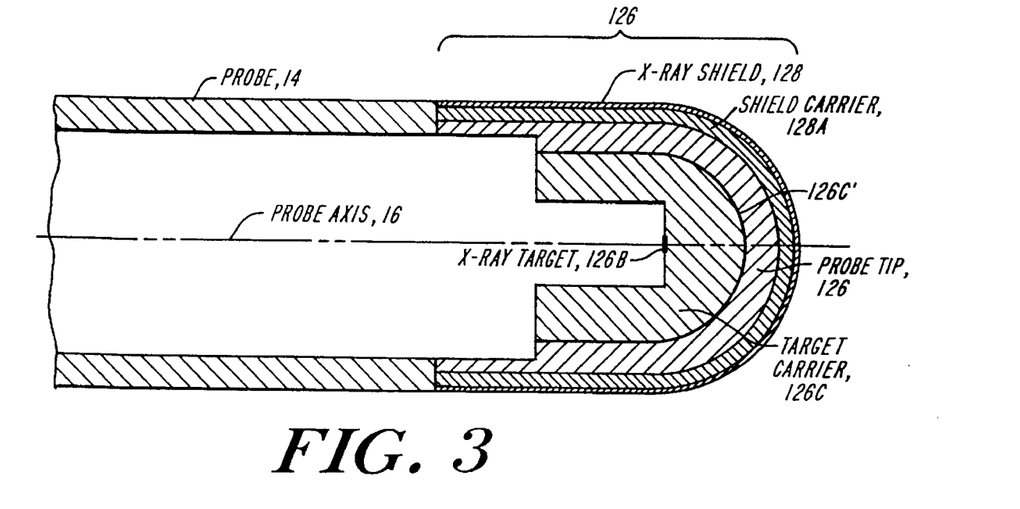
FIG. 3 is a cross-sectional view of the end of a probe having an alternate target assembly which includes an x-ray shield and x-ray target for producing a stable and reproducible source of x-rays.

The x-ray spatial distribution can also be shaped by incorporating an x-ray transmissive shield, having a variable thickness profile, into the target assembly 26. FIG. 3 shows a probe 14 having an alternate target assembly 126, for use with the x-ray apparatus 10 shown in FIG. 1, which incorporates such a shield. In the illustrative embodiment, the probe 14 is substantially similar to the probe 14 shown in FIG. 1, except for the target assembly 126. Target assembly 126 includes a probe tip 126A made of a material (e.g. Be) which is nearly transparent to x-rays, and an x-ray target 126B for generating a source of x-rays upon irradiation with an electron beam, attached to the probe 14 along a probe axis 16 at the end distal to the cathode 22 and anode 24 (shown in FIG. 1 ). In the preferred form, the outer surface of the probe tip 126A is convex, and preferably hemispherical, as in the illustrated embodiment, although other convex shapes can be used. The target assembly 126 is fabricated such that the outer diameter of the probe tip 126A is less than the outer diameter of the probe 14. A variable thickness x-ray shield (or shadow mask, as it is sometimes referred to in the art) 128 and an underlying shield carrier 128A are positioned over the probe tip 126A of the target assembly 126. At the junction of the target assembly 126 and probe 14, the outer diameter of the target assembly 126 substantially matches that of probe 14.

The x-ray shield 128 is made from a material which is not completely x-ray transparent (i.e. at least partially x-ray absorptive, such as heavy metals), and is supported by the shield carrier 128A. The x-ray flux from any point of the target assembly 126 is dependent in part upon the thickness of the x-ray shield 128 along an axis extending from the target 126B and passing through that point. Thus, in accordance with the invention, a selective restriction in thickness of the x-ray shield 128 is used to generate spatially-variable x-ray dose distributions.

Figure 4A:
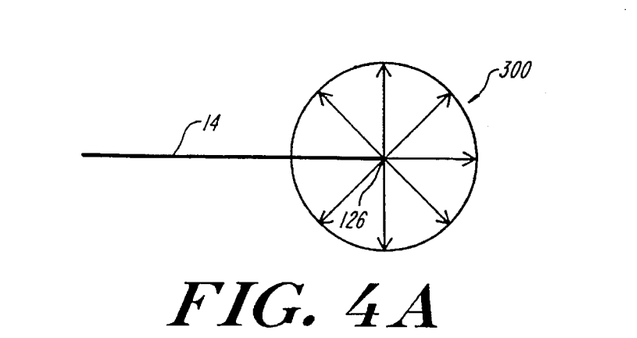
FIGS. 4A–4F show examples of various isodose contours that can be achieved with the invention.
Figure 4B:
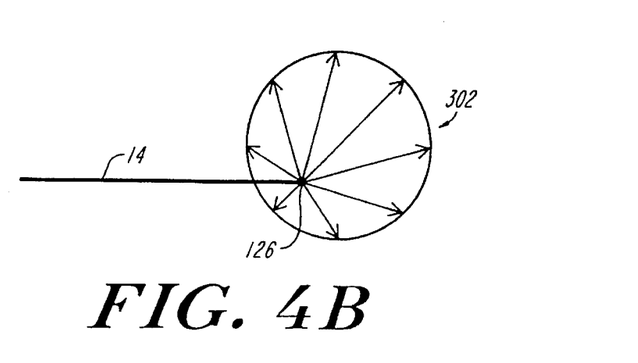
Figure 4C:
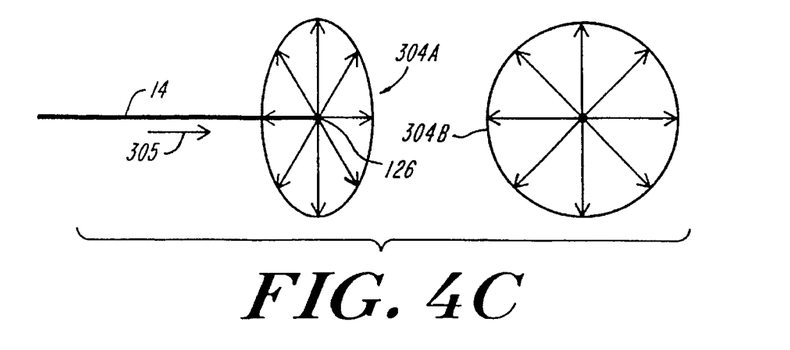
Figure 4D:
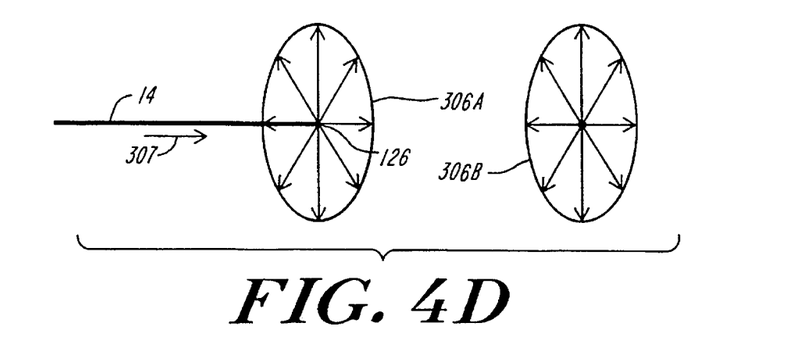
Figure 4E:
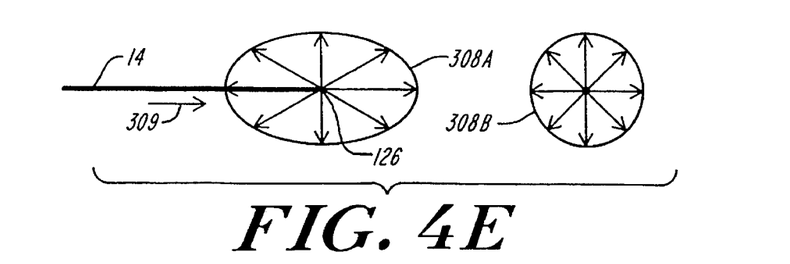
Figure 4F:
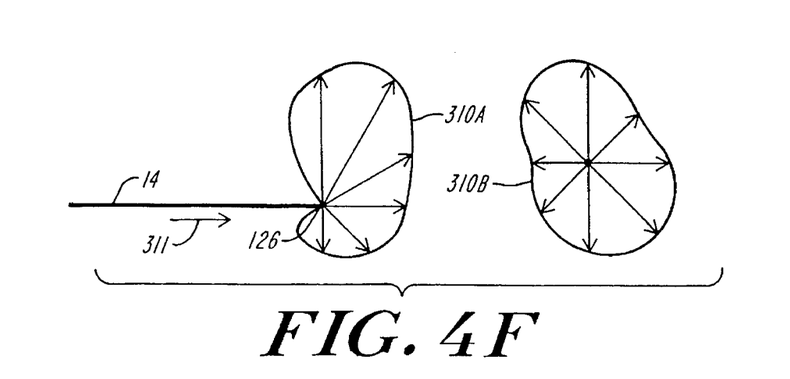

FIGS. 4A–4F depict examples of various isodose contours that can be achieved with the present invention. Specifically, FIG. 4A shows the probe 14 adapted to deliver isodose contours which form a sphere of radiation 300 centered about the probe tip 126. FIG. 4B shows the probe 14 adapted to deliver a sphere of radiation 302, wherein the probe tip 126 is offset from the center of the sphere 302. FIG. 4C shows the probe 14 having a tip 126 adapted to deliver a radiation field in the shape of an oblate ellipsoid (i.e., a "pancake" shape), as shown in perspective at 304A and looking along axis 305 at 304B. FIG. 4D depicts the probe 14 having a tip 126 adapted for delivering a radiation field in the shape of a prolate ellipsoid (i.e., a "cigar" shape), as shown in perspective at 306A and along axis 307 at 306B. As shown in FIG. 4D, the probe 14 enters the ellipsoid 306A along its minor axis. FIG. 4E shows the tip 126 also adapted for delivering a radiation field in the shape of a prolate ellipsoid. The ellipsoid is shown in perspective at 308A and along axis 309 at 308B. As can be seen, the probe 14 enters the ellipsoid 308A along its major axis. FIG. 4F depicts the probe tip 126 adapted for delivering an asymmetric radiation field shown in perspective at 310A and along axis 311 at 310B.

Broad-area radiation can be easily obtained by placing the target assembly 26 of the probe 14 at a distance from the surface to be irradiated. The solid angle of forward radiation from the target assembly 26 can be controlled with an x-ray shield as described in the above referenced patent application. The thickness of the shield at each point is determined so that a substantially uniform radiation pattern is obtained.

Another application for such a broad-area x-ray source is intracavity radiation within the body, such as the inside of the bladder. In such a case the interface between the tissue and the broad-area x-ray source can be an inflatable balloon, extending down the probe 14 so that the target assembly 26 is at the center of the balloon.

Often, when treating a body cavity with radiation therapy, it is desirable to uniformly radiate the entire surface of the soft tissue lining the cavity. In other words, it is desirable to insure that an isodose contour is coincident with the surface of the body cavity. One method of uniformly radiating the cavity is to determine the three dimensional shape of the cavity through conventional methods (e.g., by observation through a catheter, or through diagnostic procedures such as a CT scan or Magnetic Resonance Imaging) and then to fabricate a probe tip 126 that will deliver isodose contours that match the shape of the cavity. Uniform radiation is delivered to the cavity by inserting the probe, and activating it from within the body cavity. This method can be difficult to practice since body cavities rarely have a uniform shape, and further because body cavities vary in shape among individuals.

A preferred method of uniformly radiating a body cavity is to use a device to first stretch the cavity into a known, uniform shape. In the preferred embodiment for treatment of a bladder, the cavity is stretched to a spherical shape. Then, an omnidirectional x-ray generating tip of probe kit (i.e., a point source) is positioned at the center of the now spherical cavity. With that configuration, an isodose contour is coincident with the surface of the body cavity. One device useful for stretching a body cavity to a known, shape is a surgical balloon positioned at the target end of probe 14.

Figures 5, 6:
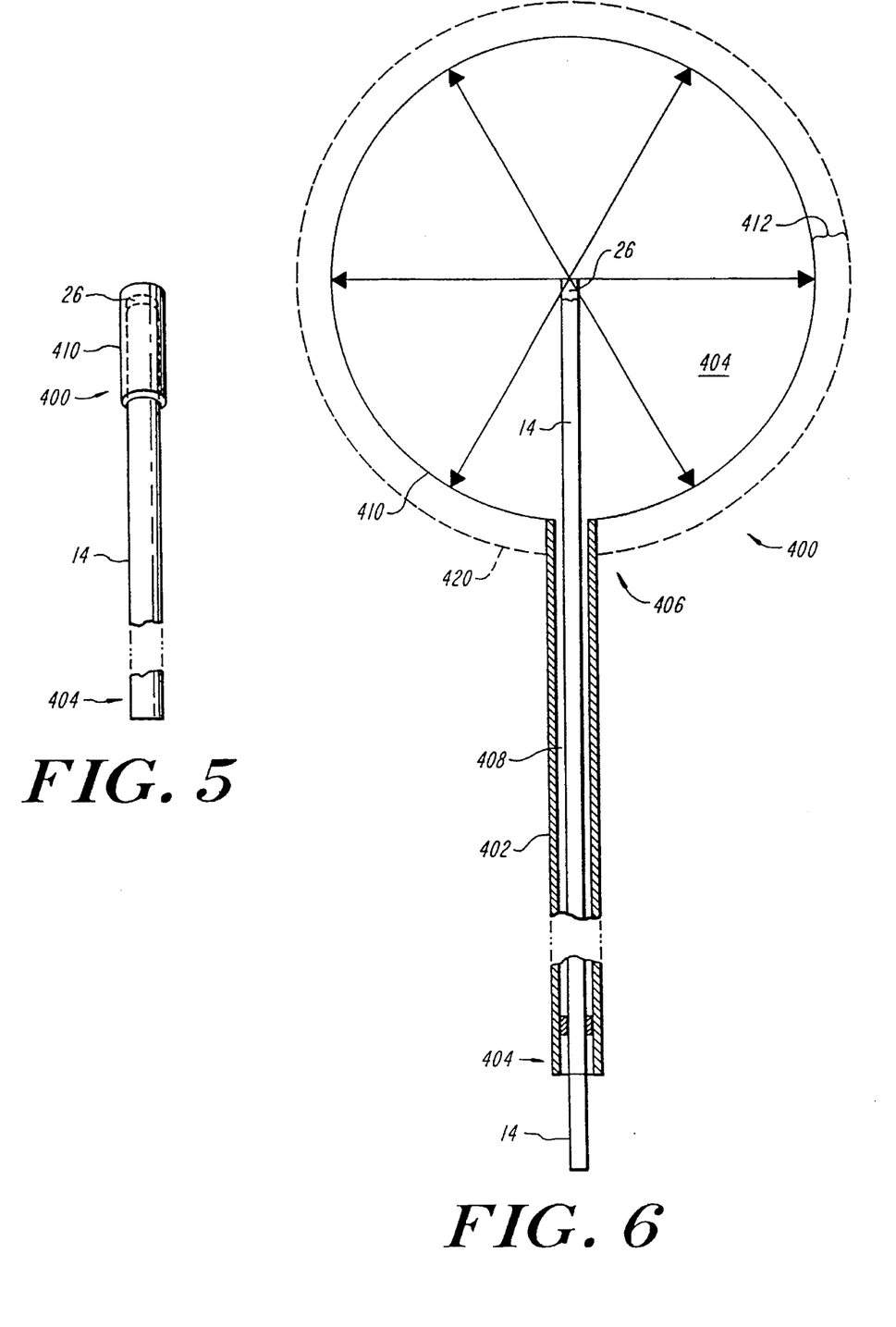
FIG. 5 shows the probe and balloon assembly of the kit of FIG. 1 with its balloon deflated.
FIG. 6 shows another embodiment of the probe and balloon assembly of the kit of the invention with its balloon inflated.

FIG. 5 shows the probe 14 of the x-ray source of FIG. 1, with a balloon assembly 400 including a balloon 410 disposed about the target assembly 26. As shown in FIG. 5, the balloon 410 is deflated and compactly folded about the target end of probe 14.

FIG. 6 shows an embodiment with a probe 14 and a balloon assembly 400 including an elongated source guidance tube 402 extending along a central axis and having a proximal end 404 and a distant end 406. The source guidance tube 402 has an interior channel 408 extending along the central axis. An inflatable balloon 410 is affixed to the outside of the distal end 406 of tube 402. The probe is slidably positionable within the tube 402 so that the target end of probe 14 is positionable within the interior region of balloon 410 when the balloon is inflated. With the balloon 410 inflated, defining a spherical region 404, as shown in FIG. 6 the target assembly 26 is substantially at the center of the balloon 410.

Inflation and deflation of balloon 410 can be controlled from proximal end 404 of probe 14, as will be discussed in detail below. Combinations of balloons and catheters are well known and are described, for example, in U.S. Pat. No. 4,209,725.

For the embodiment of FIG. 5, in practice, balloon 410 is initially deflated and packed around the distal end of probe 14, as shown in FIG. 5. The distal end 406 of probe 14, with the folded balloon 410, is then inserted into the body of the patient such that the distal end is positioned within the body cavity to be treated. Proximal end 404 remains external to the patient during the entire procedure. After distal end 406 has been inserted into the body cavity, balloon 410 is inflated to stretch the body cavity to a spherical shape.

As noted above, FIG. 6 shows balloon 410 positioned within body cavity 420 (shown in dotted lines). Body cavity 420 could be, for example, the bladder. Initially cavity 420 defines a non-uniform shape, but inflating balloon 410 stretches the lining of cavity 420 into a substantially spherical shape where the bladder provides relatively little resistance to the inflation. Preferably, after inflation, substantially all of the exterior of balloon 410 contacts the interior surface of cavity 420.

FIG. 6 also shows a channel 408 extending along probe 14, establishing a gas flow path by which the balloon 410 can be inflated from outside the patient. In the preferred embodiment, probe 14 is inserted such that target assembly 26 is positioned at the center of balloon 410. Since balloon 410 has stretched cavity 410 into a spherical shape, the center of balloon 410 is coincident with the center of the cavity 420. Accordingly, positioning target assembly 26 at the center of the inflated balloon 400 also centers target assembly 26 within the body cavity.

Once target assembly 26 is centered, the electron beam generator may be activated to direct an electron beam to be incident on target assembly 26, resulting in generation of x-radiation with an isodose contour coincident with the inflated balloon, and the lining of the deformed body cavity.

Figure 7:
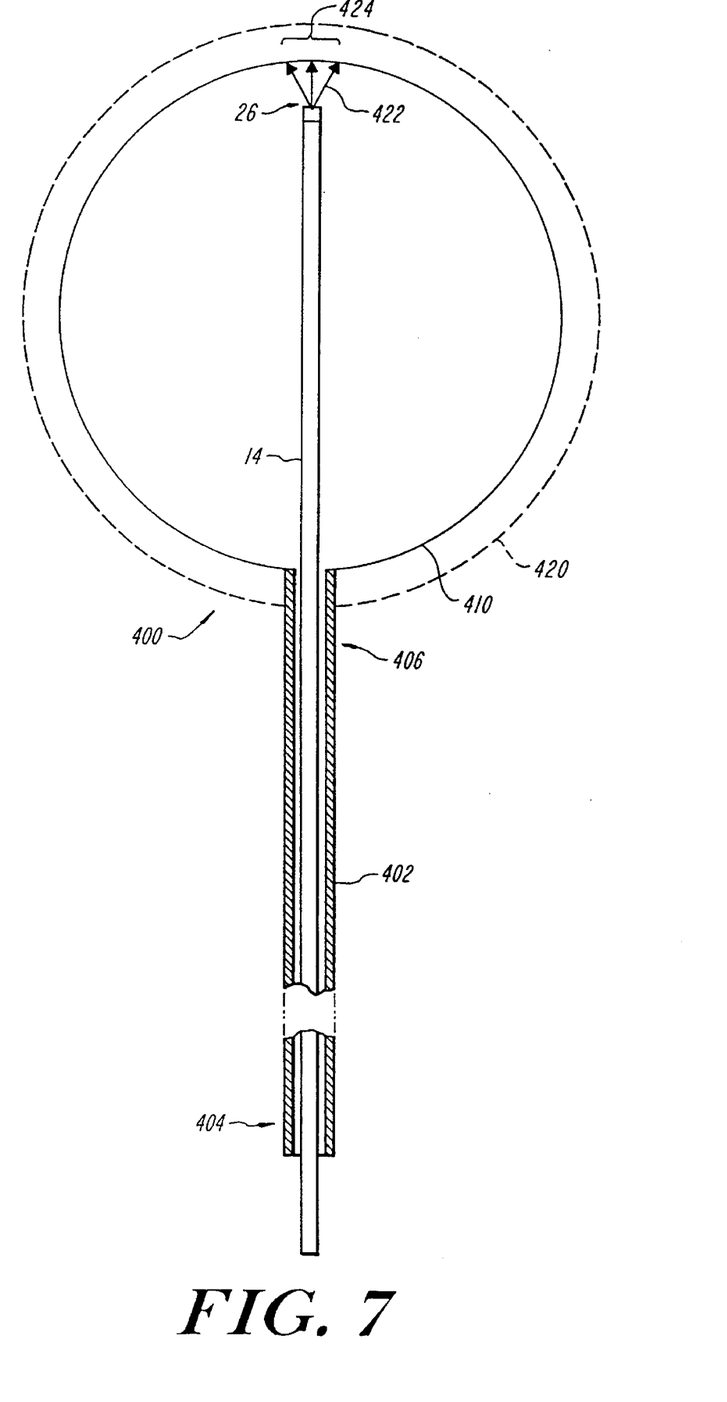
FIG. 7 shows another embodiment of the invention in which the x-ray probe is inserted to be proximal to a wall of the balloon.

FIG. 7 shows another embodiment of the invention useful for treating one section of a body cavity 420, such as a region bearing a tumor. In FIG. 7, target assembly 26 is shielded so only x-rays traveling in the direction of the forward solid angle, shown by arrows 422, are emitted from target assembly 26. In this embodiment, only region 424 of cavity 420 is radiated.

The above discussion has described the invention in connection with spherical balloons, however, as those skilled in the art will appreciate, the invention can be practiced with balloons of many shapes, including elliptical and cylindrical shapes, which can be used in treating, for example, the colon, or other internal cavities such as the urethra, vagina and cervix, uterus, colon, or rectum.

As discussed above with respect to FIG. 1, the apparatus 10 includes beam generation and acceleration components to generate and accelerate electrons, prior to those electrons entering the probe 14. The generated electron beam then flows through probe 14, impacts the target 26, and thereby produces x-rays. In the absence of magnetic fields, the electrons flowing through the probe 14 follow a straight-line trajectory. Consequently, the probe 14 is typically rigid without any bends.

However, in certain medical applications it is beneficial to use a flexible probe. One such application involves threading the x-ray source down an existing pathway, such as the trachea. Another such application involves maneuvering the x-ray source around critical structures, such as a nerves or blood vessels.

Figure 8A:
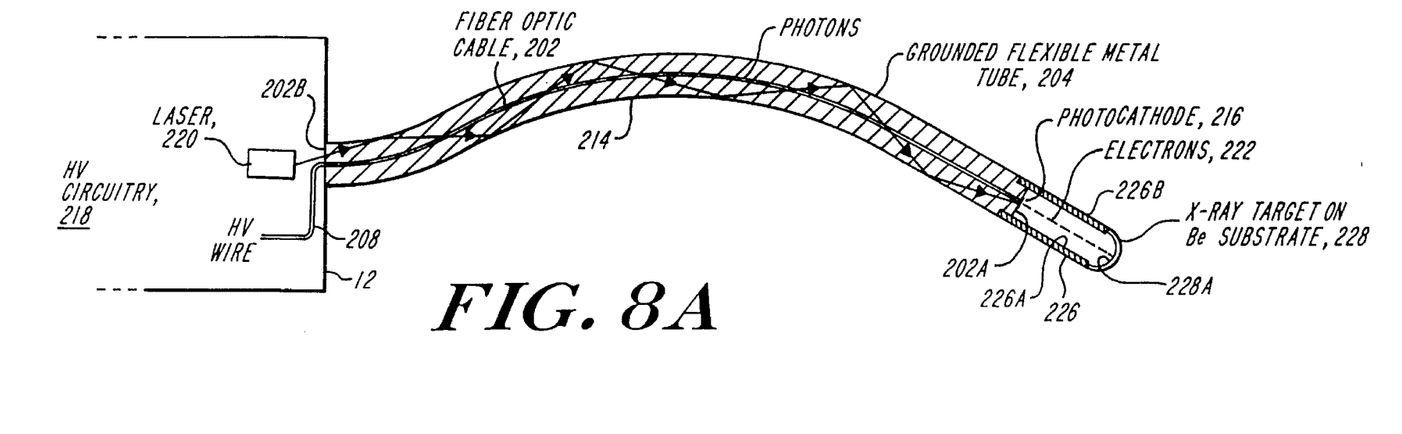
FIGS. 8A and 8B are cross-sectional views of a flexible probe which incorporates a photoemitter located within the target assembly.

FIG. 8A shows a diagram of apparatus 200 including a flexible probe 214. The apparatus 200 includes a high voltage network 218, a laser source 220, a probe assembly 214, and a target assembly 226. According to one aspect of the invention, the apparatus 200 provides the required flexibility, without using strong magnetic fields, by locating electron generating and accelerating components in the target assembly 226. The probe assembly 214 couples both the laser source 220 and the high voltage network 218 to the target assembly 226. The probe assembly includes flexible fiber optical cable 202 enclosed in a small-diameter flexible metallic tube 204.

The target assembly 226, which can be for example 1- to 2- cm in length, extends from the end of the probe assembly 214 and includes a shell which encloses the target 228. According to one embodiment, the target assembly 226 is rigid in nature and generally cylindrical in shape. In this embodiment the cylindrical shell enclosing the target assembly can be considered to provide a housing for the electron beam source as well as a tubular probe extending from the housing along the electron beam path. The inner surface 226A of the assembly 226 is lined with an electrical insulator, while the external surface 226B of the assembly 226 is electrically conductive. According to a preferred embodiment, the target assembly is hermetically sealed to the end of the probe assembly 214, and evacuated. According to another embodiment, the entire probe assembly 214 is evacuated.

The terminal end 202A of the fiber optical cable 202 is preferably coated, over at least part of its area, with a semitransparent photoemissive substance such as, Ag-O-Cs, thus forming a photocathode 216. A high voltage conductor 208, embedded in the fiber optical cable 202, conducts electrons to the cathode 216 from the high voltage network 218. Similarly, the flexible tube 204 couples a ground return from the target 228 to the high voltage network 218, thereby establishing a high voltage field between the cathode 216 and the target 228. The fiber optical cable 202 acts as an insulating dielectric between the high voltage conductor 208 and the grounded flexible tube 204.

Figure 8B:
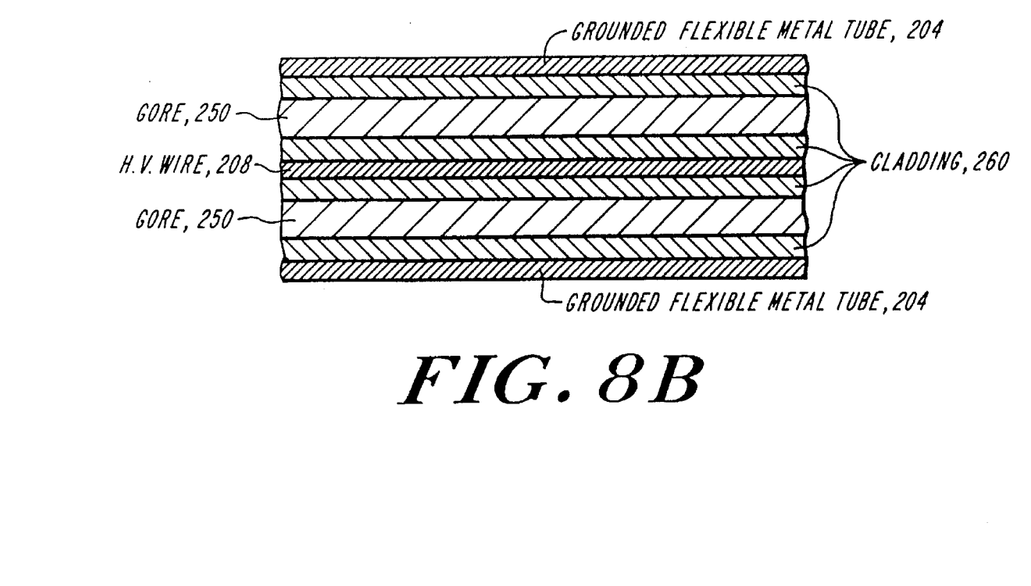

In one embodiment, to eliminate scattering of the light in the fiber optic cable 202 by the high voltage wire 208, the fiber optic cable 202 can have an annular configuration, as shown in cross-section in FIG. 8B. The light from the laser 220 travels down the annular core 250 of the fiber optic cable 202. Cladding 260 on each side of the core 250 has an index of refraction so as to refract the light beam incident on the interface back into the core 250. A grounded flexible metal tube 204 surrounds the outer cladding 260.

As in previously described embodiments, the target 228 can be for example, beryllium, (Be), coated on one side with a thin film or layer 228A of a higher impedance element, such as tungsten (W) or gold (Au).

In operation, the small semiconductor laser 220 shining down the fiber optical cable 202 activates the transmissive photocathode 216 which generates free electrons 222. The high voltage field between the cathode 216 and target 228 accelerates these electrons, thereby forcing them to strike the surface 228A of target 228 and produce x-rays. In order to generate, for example, 20 µA of current from an Ag-O-Cs photocathode 216 with a laser 220 emitting light at a wavelength of 0.8 µm, the 0.4% quantum efficiency of this photocathode 216 for this wavelength requires that the laser 220 emits 7.5 mW optical power. Such diode lasers are readily commercially available. According to the invention, the photoemissive surface which forms cathode 216 can, in fact, be quite small. For example, for a current density at the cathode 216 of 1 A/cm², the photoemitter's diameter need only be approximately 50 µm.

One difficult fabrication aspect of this invention is the fabrication of the photocathode 216, which for practical substances, with reasonable quantum efficiencies above $10^{-3}$, should be performed in a vacuum. This procedure can be carried out with the fiber optical cable 202 positioned in a bell jar, where for example, an Ag-O-Cs photosurface is fabricated in the conventional manner. Subsequently, without exposure to air, the optical cable 202 can be inserted into the tube 204. The end 202B can be vacuum sealed to the flexible tube 204.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A kit for applying x-rays to an interior surface of a body cavity, said kit comprising:
    A. an x-ray source including:
        i. a tubular element having a beam source end and a target end and defining an interior region extending along a source axis between said source end and said target end,
        ii. beam source means, disposed proximal to said beam source end, for generating an electron beam passing substantially along said source axis toward said target end,
        iii. target means, disposed proximal to said target end, for generating x-rays in response to incidence thereon of said electron beam, and
        iv. control means for selectively activating said beam source means such that said electron beam is incident on said target means, and
    B. a balloon assembly including an inflatable balloon positioned at said target end of said tubular element, and defining an interior region disposed adjacent and extending beyond said target end when inflated.

2. A kit for applying x-rays to an interior surface of a body cavity according to claim 1, wherein said balloon defines a substantially spherical interior region when inflated and said target end is positionable substantially at the center of said interior region of said balloon when inflated.

3. A kit for applying x-rays to an interior surface of a body cavity according to claim 1, wherein said x-ray source means generates an isodose contour substantially coincident with a surface contour of said balloon when said balloon is inflated.

4. A kit for applying x-rays to an interior surface of a body cavity according to claim 1, further comprising an elongated source guide tube extending along a central axis and having a proximal end and a distal end, said source guide tube defining a first interior channel extending along said central axis, wherein said balloon is affixed to the outside of said distal end of said source guide tube and
    wherein said tubular element of said x-ray source is slidably positionable within said first interior channel of said source guide tube such that said target end of said tubular element is positionable within said interior region of said balloon when said balloon is inflated.

5. A kit for applying x-rays to an interior surface of a body cavity according to claim 1, wherein said balloon defines a substantially spherical outer surface contour when inflated.

6. A kit for applying x-rays to an interior surface of a body cavity according to claim 1, wherein said control means further comprises steering means for steering said electron beam such that said beam is adjustably incident on said target end.

7. A kit for applying x-rays to an interior surface of a body cavity according to claim 1, wherein said control means further comprises means for selectively deactivating said beam source means.

8. A kit for applying x-rays to an interior surface of a body cavity according to claim 1, further comprising inflation means for selectively inflating and deflating said balloon.

9. A kit for applying x-rays to an interior surface of a body cavity according to claim 1, wherein said inflation means includes an interior channel, disposed in said tubular element and extending from said beam source end to a point near said target end, said interior channel being in communication to a region interior to said balloon.

10. A kit for applying x-rays to an interior surface of a body cavity according to claim 9, wherein said inflation means further comprises a selectively operative pump disposed near said end and coupled to said interior channel.

11. A method for applying x-rays to an interior surface of a body cavity comprising the steps of:
    A. providing an x-ray source including:
        i. a tubular element having a beam source end and a target end and defining an interior region extending along a source axis between said source end and said target end, ii. beam source means, disposed proximal to said beam source end, for generating an electron beam passing substantially along said source axis toward said target end, iii. target means, disposed proximal to said target end, for generating x-rays in response to incidence thereon of said electron beam, and iv. control means for selectively activating said beam source means such that said electron beam is incident on said target means, and B. providing a balloon assembly including an inflatable balloon positioned at said target end of said tubular element, and defining an interior region adjacent to and extending beyond said target end when inflated, C. inserting said tubular element into the body such that said target end occupies a predetermined location within said body cavity, D. inflating said balloon, E. operating said control means such that said electron beam is incident on said target, thereby generating said x-rays.

12. A method for applying x-rays to an interior surface of a body cavity according to claim 11, wherein said balloon defines a substantially spherical interior region when inflated, and wherein said step of inserting said tubular element includes a step of positioning said target end substantially at the center of said balloon interior region.

13. A method for applying x-rays to an interior surface of a body cavity according to claim 11, wherein said inflating step includes a step of inflating said balloon such that substantially all of a surface of said balloon contacts the interior of the body cavity.

14. A method for applying x-rays to an interior surface of a body cavity according to claim 13, wherein said inflating step further includes a step of stretching the surface of the body cavity to a substantially uniform shape.

15. A method for applying x-rays to an interior surface of a body cavity according to claim 13, wherein the inflating step further includes a step of stretching the surface of the body cavity to a substantially spherical shape.

16. A kit for applying x-rays to an interior surface of a body cavity, said kit comprising:

A. an x-ray source including:
i. a tubular element having a beam source end and a target end and defining an interior region extending along a source axis between said source end and said target end, said tubular element having an outer diameter D1, ii. beam source means, disposed proximal to said beam source end, for generating an electron beam passing substantially along said source axis toward said target end, iii. target means, disposed proximal to said target end, for generating x-rays in response to incidence thereon of said electron beam, and iv. control means for selectively activating said beam source means such that said electron beam is incident on said target means, and B. a source guidance tube extending along a central axis and having a proximal end and a distal end, said tubular element defining an interior channel extending along said central axis, said interior channel having an inner diameter D2.

C. a balloon assembly including an inflatable balloon positioned at the distal end of said source guidance tube, and defining an interior region disposed adjacent and extending beyond said distal end when inflated, wherein D2 is greater than D1, whereby said target end of said tubular element of said X-ray source is slidably positionable within and beyond said distal end of said interior channel of said source guidance tube, and into said interior region of said balloon.

17. A kit for applying x-rays to an interior surface of a body cavity according to claim 16, wherein said balloon defines a substantially spherical interior region when inflated and said target end is positionable substantially at the center of said interior region of said balloon.

18. A kit for applying x-rays to an interior surface of a body cavity according to claim 16, wherein said x-ray source means generates an isodose contour substantially coincident with a surface contour of said balloon when said balloon is inflated.

19. A kit for applying x-rays to an interior surface of a body cavity according to claim 16, wherein said balloon defines a substantially spherical outer surface contour when inflated.

20. A kit for applying x-rays to an interior surface of a body cavity according to claim 16, wherein said control means further comprises steering means for steering said electron beam such that said beam is adjustably incident on said target end.

21. A kit for applying x-rays to an interior surface of a body cavity according to claim 16, wherein said control means further comprises means for selectively deactivating said beam source means.

22. A kit for applying x-rays to an interior surface of a body cavity according to claim 16, further comprising inflation means for selectively inflating and deflating said balloon.

23. A kit for applying x-rays to an interior surface of a body cavity according to claim 16, wherein said inflation means includes an interior channel, disposed in said tubular element and extending from said beam source end to a point near said target end, said interior channel being in communication to a region interior to said balloon.

24. A kit for applying x-rays to an interior surface of a body cavity according to claim 23, wherein said inflation means further comprises a selectively operative pump disposed near said end and coupled to said interior channel.

* * * * *